United States Patent
Herwig et al.

(10) Patent No.: US 7,253,329 B2
(45) Date of Patent: Aug. 7, 2007

(54) SELECTIVE HYDROGENATION OF CYCLODODECATRIENE TO CYCLODODECENE

(75) Inventors: Juergen Herwig, Huenxe (DE); Norbert Wilczok, Muelheim (DE); Martin Roos, Haltern am See (DE); Rudolf Burghardt, Recklinghausen (DE); Johann Gaube, Rossdorf (DE); Georg Oenbrink, Duelmen (DE); Bernd Guenzel, Haltern am See (DE)

(73) Assignee: Degussa AG, Duesseldorf (DE)

( * ) Notice: Subject to any disclaimer, the term of this patent is extended or adjusted under 35 U.S.C. 154(b) by 522 days.

(21) Appl. No.: 10/790,094

(22) Filed: Mar. 2, 2004

(65) Prior Publication Data

US 2004/0225168 A1     Nov. 11, 2004

(30) Foreign Application Priority Data

Mar. 8, 2003    (EP)    ................... 03005208

(51) Int. Cl.
*C07C 5/05*     (2006.01)
*C07C 5/03*     (2006.01)

(52) U.S. Cl. ...................... 585/273; 585/259; 585/276; 585/277

(58) Field of Classification Search ................ 585/273, 585/259, 276, 277
See application file for complete search history.

(56) References Cited

U.S. PATENT DOCUMENTS 5,177,278 A * 1/1993 Sanchez ..................... 585/275

OTHER PUBLICATIONS

Georg Wiessmeier, et al., "Heterogeneously Catalyzed Gas-Phase Hydrogenation of cis, trans, trans-1,5,9-Cyclododecatriene on Palladium Catalysts Having Regular Pore Systems", Ind. Eng. Chem. Res., vol. 35, No. 12, XP-002246783, 1996, pp. 4412-4416.
Georg Wiessmeier, et al., "Heterogen katalysierte Selektivhydrierung von cis, trans, trans-1,5,9-Cyclododecatrien an einem Pd/Al$_2$O$_3$-Schalenkatalysator", Chem. Ing. Tech., vol. 67, No. 1, XP-000485565, 1995, pp. 78-80.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

A process for preparing cyclododecene by selective gas-phase hydrogenation of at least one starting material selected from cyclododecatriene, cyclododecadiene and mixtures thereof, wherein the starting material present in the gas phase is hydrogenated in the presence of a catalyst in a fixed-bed reactor and the Bodenstein number for the process is greater than 100.

32 Claims, No Drawings

SELECTIVE HYDROGENATION OF CYCLODODECATRIENE TO CYCLODODECENE

BACKGROUND OF THE INVENTION

1. Field of the Invention

The present invention relates to a process for the gas-phase hydrogenation of cyclododecatriene and/or cyclododecadiene to cyclododecene over a solid catalyst comprising a catalytically active metal of group VIII of the Periodic Table of the Elements.

2. Description of the Invention

The selective hydrogenation of cyclododecatriene to cyclododecene has frequently been described in the literature, and numerous attempts have been made to carry out selective hydrogenation with a high degree of conversion and high selectivity.

According to prevailing opinion, the hydrogenation of cyclododecatriene (hereinafter referred to as CDT), which is predominantly in the form of cis,trans,trans-1,5,9-cyclododecatriene, occurs stepwise via dienes, predominantly trans,trans-1,5-cyclododecadiene and cis,trans-1,5-cyclododecadiene (both hereinafter referred to as CDD) and the isomer mixture of trans- and cis-cyclododecene (hereinafter referred to as CDEN) corresponding virtually to the equilibrium to cyclododecane (hereinafter referred to as CDAN).

Since doubly unsaturated compounds such as CDD lead to formation of relatively high-boiling fractions in subsequent reactions such as hydroformylations or hydrations, the degree of conversion of CDD and CDT to CDEN is desirably greater than 99.0%. The selectivity of CDEN formation relative to all products should be above 90% so that the space-time yield in subsequent reactions of CDEN is not reduced by the amount of inert CDAN formed.

One possible way of achieving a high yield of CDEN is homogeneous selective hydrogenation using Ru complexes. U.S. Pat. No. 5,180,870 describes the homogeneous hydrogenation of CDT using Ru complexes. Here, sterically hindered amines and free triarylphosphine are added in order to partially poison the catalyst. Separation of the CDEN from the catalyst and the amines is difficult and leads to potential contamination of the CDEN product with amines. In the patents U.S. Pat. No. 5,177,278, U.S. Pat. No. 3,804,914, U.S. Pat. No. 5,210,349, and U.S. Pat. No. 5,128,296, solvents are added to the homogeneous hydrogenation of CDT with Ru complexes. This leads to low space-time yields and problems in the separation of catalyst and solvent from the reaction product. U.S. Pat. No. 6,194,624 describes homogeneous hydrogenation likewise using a ruthenium catalyst with addition of carbon monoxide and carboxylic acids such as acetic acid or propionic acid. Here too, the separation of the CDEN from the homogeneous catalyst and the carboxylic acid is problematical.

Processes for the heterogeneously catalyzed preparation of CDEN have also been described in the literature. Palladium catalysts are particularly suitable for this heterogeneous catalysis.

In addition, studies using activated copper on an oxidic support have also been reported. The results obtained using copper catalysts which have been presented by Castro et al. in Stud. Surf. Sci. Catal. (1991), 63 (Prep. Catal. V), 95–102 show a notable selectivity to CDEN but only a very low activity. Furthermore, both the selectivity and the activity are dependent to a considerable degree on the preparation and quality of the catalyst system. Industrial use of these catalysts is therefore very difficult since reproducibility of the results is not guaranteed.

The heterogeneous preparation of CDEN may be carried out by, for example, batchwise hydrogenation in the liquid phase using a suspended catalyst, continuous three-phase hydrogenation in a fixed bed (CDT in the liquid phase) and continuous gas-phase hydrogenation over a fixed bed (CDT in the gas phase).

U.S. Pat. No. 3,400,164 and U.S. Pat. No. 3,400,166 and GB 19680712 describe a batchwise hydrogenation in the liquid phase using a suspended catalyst and show that a CDEN selectivity of about 94% can be achieved at a high CDT/CDD conversion when using a palladium catalyst on a support (5% Pd on activated carbon). 1.4 g of this catalyst are used per 100 g of CDT. The reaction is carried out at 160° C. The hydrogen pressure is maintained at 2.07 bar until 75% of the total hydrogen used has been consumed, then at 0.69 bar to a hydrogen consumption of 90% and finally at 0.345 bar. The hydrogenation is then complete after about one hour. Based on the mass of palladium used, the average throughput is 71 g (CDT)/g (Pd)·h.

A disadvantage of this slurry variant of a batch process is the removal of the catalyst, particularly when it has been abraded after some time. A subsequent filtration step complicates the process and inevitably leads to losses in yield.

In addition, the patents U.S. Pat. No. 3,400,164 and U.S. Pat. No. 3,400,166 indicate that aromatic cyclic compounds are formed to an increased extent as by-products at elevated temperatures above 160° C. The patent documents U.S. Pat. No. 3,400,165 and DE 1 678 829 state that these aromatic compounds are formed from CDT. These aromatic by-products are difficult to separate from the desired product and require an increased outlay for purification. For this reason, a process is carried out at 160° C. to provide a very high conversion of CDT and the further conversion of the resulting CDD is carried out at a significantly higher temperature. These aromatic by-products are difficult to separate off and require an increased outlay for purification.

Furthermore, batch processes are generally not suitable for large-scale industrial production and only acceptable when there is no economically viable alternative. Adopting a hydrogenation using a suspended catalyst into a continuous process would raise considerable difficulties and would also be complicated since the characteristics of a plug flow reactor are desirable for subsequent reactions and formation of the intermediate target product. This would require a reactor cascade having a relatively large number of stirred vessels. After each stirred vessel, the catalyst would have to be separated from the outflowing product and returned to the stirred vessel. Such a procedure is therefore difficult to carry out on an industrial scale.

Alternatives may include a trickle-bed reactor in which CDT in liquid form is passed over a fixed bed of palladium-coated pellets in the presence of hydrogen and a fixed-bed process where the liquid and gas are introduced from the bottom. Experiments using such reactors/procedures are described in Catal. Today (F. Stueber et al., 1995, 24(1–2), 95–101) and in Chemical Engineering Science (R. V. Chaudhari, 2001, 65(2), 557–564). In the experiments described in Catal. Today, a coated catalyst having a palladium-containing coating thickness of 240 μm and a hydrogen pressure of 1.5–12 bar were employed. When the reactants were introduced from the bottom, a CDEN yield of only 70% at a (CDT+CDD) conversion of 85% was achieved. It was found in this case that activity problems arise because of diffusion and transport phenomena which are due to the choice of a three-phase system of solid/liquid/gas. The authors identified liquid/solid mass transfer as the limiting factor.

Furthermore, the experiments using a fixed-bed or trickle-bed catalyst displayed a low selectivity with regard to the simultaneous formation of CDAN, as indicated by the significant formation of CDAN occuring at the maximum CDEN formation.

In addition, the downflow and upflow modes are compared in the article in Chemical Engineering Science, with a somewhat higher selectivity being found in the case of the latter. The hydrogen pressure was 12 bar. The yields of CDEN reported were not above 35%. The low yields show that industrial implementation of this process may not be viable.

Gas-phase hydrogenation of cyclododecatriene is known from Wieβmeier (Ind. Eng. Chem. Res. (1996), 35(12), 4412–4416) where a specially produced monolithic microstructure reactor having microchannels and uniform mesopore systems is employed. This reactor is produced by generating a uniform oxidic layer having a thickness of 20–50 μm, depending on the electrolysis time, on structured aluminum wire by anodic oxidation. This layer has pores of uniform length, uniform diameter and uniform spacing aligned perpendicular to the surface in a hexagonal pattern (i.e. the layer thickness is constant). The pores are closed at one end at the oxide/aluminum interface. The pores are repeatedly impregnated with the solution of a Pd compound, dried, calcined and finally reduced so that these pores become uniformly coated with Pd crystallites (degree of dispersion about 0.2–0.3).

Use of this reactor makes it possible to achieve a conversion of more than 96% and a selectivity to cyclododecene of 88%. At the same time, 8% of CDAN was formed and the throughput per amount of catalyst was 36 g (CDT)/g(Pd)·h.

This reactor system is disadvantaged in that the production of the catalyst is very complicated and such a system is therefore unsuitable for industrial production of cyclododecene.

Furthermore, this article states that commercial catalysts comprising a support material with very fine noble metal particles dispersed therein cannot be used for the gas-phase hydrogenation of cyclododecatriene. The nonuniform distribution of the pores on the surface of these conventional supports and the associated nonuniformity of the active metal species on the surface increase the mass transfer problems which are primarily responsible for the poor activity of the catalyst in the article. The authors rule out the industrial use of commercial catalysts.

SUMMARY OF THE INVENTION

Accordingly, it is object of the invention to find a gas-phase process for the heterogeneous hydrogenation of cyclododecatriene and/or cyclododecadiene (e.g., the starting materials) to cyclododecene, which is preferably operated continuously, gives a high CDEN selectivity at a conversion (CDT+CDD) of over 99.5% and can be carried out on an industrial scale, free of the disadvantages of the processes described hitherto, and utilizes a readily available catalyst.

According to the invention, this object is achieved by a process for preparing cyclododecene by selective gas-phase hydrogenation of at least one starting material such as cyclododecatriene, cyclododecadiene and mixtures thereof in a fixed-bed reactor, wherein the Bodenstein number for the process in the fixed-bed reactor is greater than 100.

DETAILED DESCRIPTION OF THE INVENTION

It has surprisingly been found that an industrial process for the heterogeneous gas-phase hydrogenation of CDT and/or CDD to CDEN over a catalyst at very low hydrogen pressures can be realised according to the present invention. Despite intensive research, such a process was not known hitherto. It was even stated in Ind. Eng. Chem. Res. (1996), 35 (12), 4412–4416, that specific microstructured catalysts are necessary to achieve a high CDEN selectivity.

Apart from cyclododecatriene, it is also possible for further cyclic, nonaromatic, multiply unsaturated hydrocarbons, for example cyclooctadiene or trimethylcyclododecatriene, to be hydrogenated selectively by the process of the invention.

The Bodenstein number is a reaction-kinetic index for the residence time distribution in a real flow tube according to the dispersion model. It is a measure of backmixing. In addition, the Reynolds number is often reported as a further index for a catalytic process. It reflects the flow state. Definitions of the Bodenstein number and the Reynolds number may be found, for example in the book "Chemische Reaktionskinetik" by Baems et al., Thieme Verlag, 1987. According to this reference, the Bodenstein number is defined as the product of the mean flow velocity $\bar{u}$ and the length of the flow tube L divided by the axial diffusion coefficient $D_{ax}$.

$$Bo = \frac{\bar{u}L}{D_{ax}} = Pe_{ax} \cdot \frac{L}{d_R}$$

Pe=Peclet number

In a preferred embodiment, the Bodenstein number in the process of the invention is greater than 500, in particular greater than 1,000. Numbers between 500 and 1,000 are included for example 600, 700, 800 and 900 as are multiples thereof such as 1,500, 1,400, 1,600, 2,000 etc.

When these parameters are met the heterogeneous reaction of gaseous cyclododecatriene and/or CDD with hydrogen in the presence of a solid catalyst can provide improved selectivities for the formation of cyclododecene from cyclododecatrienes.

The Reynolds number in the process of the invention is preferably greater than 10. The Reynolds number is more preferably greater than 100 and particularly preferably greater than 200. An improved CDEN selectivity (more than 90%) can be achieved in this way. Numbers between 10 and 100 are included for example 20, 30, 40, 50, 60, 70, 80 and 90 and multiples and/or fractions thereof.

In a further, preferred embodiment of the present invention, the starting material present in the gas phase is hydrogenated in the presence of a shaped body.

Such a shaped body may preferably comprise more than 90% by weight of support material, based on the total weight of the shaped body. The use of a shaped body makes it possible to carry out the heterogeneous process of the invention with catalysts that are easier to produce and also to ensure that industrial implementation can be achieved.

The catalyst used in the process of the invention is a supported catalyst whose active component is a metal of transition group VIII of the periodic table of the elements, preferably palladium. Preferred supports are aluminum oxide, silicon oxide, titanium dioxide and zirconium dioxide, preferably γ-aluminum oxide. In a process according to the present invention, particular preference is given to coated catalysts in which the distribution of the catalytically active metal in the shaped body is not homogeneous and wherein the catalyst is present on a non-metallic support. Such catalysts can be produced by impregnating the outer region of the support pellet with the metal or by coating a nonporous core of, for example, aluminum oxide and impregnating this layer with the metal. The palladium content is from 0.05 to 5.0% by mass, based on the total catalyst pellet, preferably from 0.5 to 1.0% by mass. The thickness of the outer layer of the shaped catalyst body is not more than 1/10 of the maximum dimension of the shaped body and more than 70% by weight of the active metal of the shaped body is present in this outer layer.

In a further, preferred embodiment of the present invention, the shaped body is essentially round; in particular, it is spherical. This geometry results in an effective ratio of the mass of the catalyst to be used and the surface provided with active metal.

The shaped body may have a diameter of more than 0.5 mm, in particular more than 2 mm. In general, the shaped bodies are present in a fixed bed. This way of carrying out the reaction makes it possible for product and catalyst to be separated easily.

The throughput per amount of catalyst used in the process of the invention is defined as mass of starting material/mass of Pd·h. It is preferably from 15 to 500 g, particularly preferably from 20 to 100 g, of starting material/g of Pd·h and in addition to the indices Bodenstein number and Reynolds number is an important process variable. Numbers between the stated values are included for example multiples and fractions of the stated numbers such as 30, 45, 40, 80, 75, 200, 150, 250 etc.

In the process of the invention, the starting material is vaporized into a stream of circulating gas. This circulating gas preferably consists essentially of inert gas such as nitrogen, methane, carbon dioxide, helium, neon, argon, krypton, xenon or mixtures of these gases, preferably nitrogen. The partial pressure of the CDT in the circulating gas stream should be set so that it is below the saturation vapor pressure of CDT at the reaction temperature, preferably from 50 to 80% of the saturation pressure. The partial pressure of hydrogen in the circulating gas is, according to the invention, set so that a conversion of (CDT+CDD) of at least 99% is obtained. In steady-state operation of the plant, further hydrogen may be introduced in an amount corresponding to the amount consumed. The total pressure of the circulating gas is not critical to the process and is preferably from 50 to 10,000 kPa.

To increase the CDEN selectivity, the introduction of hydrogen can be divided so that only part of the hydrogen is fed in at the reactor inlet and the remainder is fed in elsewhere in the reactor. Preference is given to feeding in two thirds of the total amount of hydrogen at the reactor inlet and the remainder at a point in the reactor at which CDT has largely been reacted. The total molar amount of hydrogen is preferably from 0.9 to 1.2 times the amount which is theoretically required to hydrogenate the cyclododecatriene and/or cyclododecadiene present in the starting material to cyclododecene.

A further increase in the selectivity to CDEN can be achieved by introducing carbon monoxide as reaction gas. The partial pressure of the carbon monoxide, measured at the reactor outlet, can be varied in the range from 10 to 1,000 Pa.

The reaction temperature can be varied within wide limits. Preference is given to a reaction temperature of from 90 to 180° C., particularly preferably in the range from 100 to 160° C. The temperature of the reactor does not have to be constant but can be varied within the above-mentioned limits. It is possible to set a rising or falling temperature profile in the reactor.

As reactor, it is possible to use a fixed-bed reactor whose diameter/length ratio is chosen so that it has largely plug flow characteristics and thus has little backmixing. Its diameter/length ratio is preferably from 0.03 to 0.38. A further suitable type of reactor is a shell-and-tube reactor, especially a tube-and-shell reactor where a bundle of tubes is present in the shell, without implying any restriction of the invention to these types of reactor.

In a particularly preferred embodiment of the present invention, the process for the selective hydrogenation of cyclododecatriene and/or cyclododecadiene is carried out continuously.

The invention is illustrated by the following examples which are not intended to limit the claimed process for the embodiments described herein.

EXAMPLE 1 (COMPARATIVE)

This example has been taken from the thesis by Dipl. Ing. Georg F. L. Wießmeier having the title: "Monolithische Mikrostruktur-Reaktoren mit Mikroströmungskanälen und regelmäßigen Mesoporensystemen für selektive, heterogen katalysierte Gasphasenreaktionen" Shaker Verlag 1997, ISBN 3-8265-2183-8.

A tubular reactor having a diameter of 8.5 mm was charged with 0.16 g of the Heraeus catalyst K-0240 (0.5% Pd on aluminum oxide) which had been comminuted to a mean particle size of 400 μm. At a bed density of about 1 g/cm$^3$, the bed height was 2.8 mm. A volume flow of 8.6 l/h was then set, giving a flow velocity of 0.04 m/s. The total pressure was 110 kPa, the cyclododecatriene (CDT) pressure was 110 Pa, the hydrogen pressure was 330 Pa (remainder: nitrogen) and the reaction temperature was 120° C. From this data, it is possible to calculate a particle-based Reynolds number $Re_p$=0.7 and, at an axial particle-based Peclet number $Pe_{ax,p}$=2, a Bodenstein number Bo=14. A maximum selectivity of 62% of CDEN at a CDT conversion of 80% was achieved under these conditions. This shows that at low Bodenstein numbers, which equates to high backmixing, only low selectivities can be achieved in the selective hydrogenation of cyclododecatriene to cyclododecene.

EXAMPLE 2 (ACCORDING TO THE INVENTION)

A coated catalyst comprising 0.5% of Pd on aluminum oxide and having a mean particle diameter of 2.5 mm was introduced in a 2 m high bed into a tube reactor having a cross-sectional area of 1.46 m$^2$. At a flow velocity of 1.58 m/s, the particle-based Reynolds number $Re_p$ is 247 and, at an axial particle-based Peclet number $Pe_{ax,p}$=2, the Bodenstein number Bo is 1,600. Under these conditions, a selectivity of 90% of CDEN was achieved at a CDT conversion of 100% at 120° C. and otherwise at the same pressure and concentration ratios as in example 1. The residual CDD content was 0.2%. The total conversion of (CDT+CDD) was thus 99.8%.

This shows that at high Bodenstein numbers, which equates to low backmixing, it is possible to achieve significantly higher selectivities in the selective hydrogenation of cyclododecatriene to cyclododecene.

EXAMPLE 3 (ACCORDING TO THE INVENTION)

The procedure of example 2 was repeated, but 3,000 ppm of carbon monoxide were additionally mixed into the reaction gas. A selectivity of 94% of CDEN at a CDT conversion of 100% was achieved in this way. The residual CDD content was 0.2%. The total conversion of (CDT+CDD) was thus 99.8%.

This example clearly shows that a further increase in the selectivity is achieved by addition of carbon monoxide to the reaction gas.

The entire contents of European Patent Application No. 03005208.8, filed on Mar. 8, 2003, are incorporated herein by reference.

Obviously, numerous modifications and variations of the present invention are possible in light of the above teachings. It is therefore to be understood that within the scope of the appended claims, the invention may be practiced otherwise than as specifically described herein.

The invention claimed is:

1. A process for preparing cyclododecene, comprising:
contacting at least one starting material selected from the group consisting of cyclododecatriene, cyclododecadiene and mixtures thereof, in the gas-phase with a catalyst in a fixed-bed reactor in the presence of hydrogen, thereby preparing said cyclododecene product,
wherein the Bodenstein number in the fixed-bed reactor is greater than 100.

2. The process as claimed in claim 1, wherein the Bodenstein number for the process in the fixed-bed reactor is greater than 500, in particular greater than 1000.

3. The process as claimed in claim 1, wherein the Reynolds number is greater than 10.

4. The process as claimed in claim 1, wherein the throughput per amount of catalyst is ranges from 15 to 500 g, of at least one starting material selected from the group consisting of cyclododecatriene, cyclododecadiene and mixtures thereof per gram of Pd·h.

5. The process as claimed in claim 1, wherein the catalyst is in the form of a shaped body.

6. The process as claimed in claim 1, wherein the catalyst is in the form of a shaped body and the shaped body comprises more than 90% by weight of support material, based on the total weight of the shaped body.

7. The process as claimed in claim 1, wherein the catalyst is in the form of a shaped body and the shaped body is essentially round.

8. The process as claimed in claim 1, wherein the catalyst is in the form of a shaped body and has a diameter of more than 0.5 mm.

9. The process as claimed in claim 1, wherein the catalyst is present on a support material and is in the form of a shaped body comprising γ-aluminum oxide.

10. The process as claimed in claim 1, wherein the catalyst is present on a non-metal support material.

11. The process as claimed in claim 1, wherein the catalyst is in the form of a shaped body and comprises at least one finely divided, catalytically active metal of group VIII of the Periodic Table of the Elements.

12. The process as claimed in claim 1, wherein the distribution of the catalytically active metal in the shaped body is not homogeneous.

13. The process as claimed in claim 1, wherein the shaped body has an outer layer having a thickness of not more than 1/10 of the maximum dimension of the shaped body, and more than 70% by weight of the catalytically active metal is present in this layer.

14. The process as claimed in claim 1, wherein the catalyst comprises catalytically active palladium.

15. The process as claimed in claim 1, wherein the molar amount of hydrogen ranges from 0.9 to 1.2 times the amount required to hydrogenate the theoretical amount of cyclododecatriene and cyclododecadiene to cyclododecene.

16. The process as claimed in claim 1, wherein the contacting is carried out at a temperature in the range of 90 to 180° C.

17. The process as claimed in claim 1, wherein the contacting is carried out under an inert gas.

18. The process as claimed in claim 1, wherein the contacting is carried out in the presence of hydrogen and carbon monoxide.

19. The process as claimed in claim 1, wherein the contacting is carried out in the presence of hydrogen, carbon monoxide and at least one inert gas.

20. The process as claimed in claim 1, further comprising:
vaporizing the starting material in an inert gas atmosphere.

21. The process as claimed in claim 1, wherein the total pressure in the gas phase ranges from 50 to 10,000 hPa.

22. The process as claimed in claim 1, which is carried out continuously.

23. The process as claimed in claim 1, wherein the Bodenstein number is greater than 1,000.

24. The process as claimed in claim 1, wherein the Reynolds number is greater than 100.

25. The process as claimed in claim 24, wherein the Reynolds number is greater than 200.

26. The process as claimed in claim 1, wherein the throughput per amount of catalyst ranges from 20 to 100 gm of at least one of cyclododecatriene or cyclododecadiene/g Pd·h.

27. The process as claimed in claim 1, wherein the catalyst is in the form of a spherical shaped body.

28. The process as claimed in claim 1, wherein the catalyst is in the form of a shaped body having a diameter of more than 2 mm.

29. The process as claimed in claim 1, wherein the contacting is carried out at a temperature in the range of 100 to 160° C.

30. The process as claimed in claim 1, wherein the contacting is carried out in the presence of hydrogen and an inert gas comprising nitrogen.

31. The process as claimed in claim 1, wherein the contacting is carried out in the presence of hydrogen and an inert gas comprising nitrogen and carbon monoxide.

32. The process as claimed in claim 1, which is carried out under plug flow conditions.

* * * * *